United States Patent [19]

Davy et al.

[11] 4,126,679

[45] Nov. 21, 1978

[54] COSMETIC STICK

[75] Inventors: Peter F. Davy, Scottsdale, Ariz.;
Michael L. Drolet, Crystal Lake, Ill.

[73] Assignee: Armour-Dial, Inc., Phoenix, Ariz.

[21] Appl. No.: 757,405

[22] Filed: Jan. 6, 1977

Related U.S. Application Data

[60] Continuation-in-part of Ser. No. 655,665, Feb. 5, 1976, abandoned.

[51] Int. Cl.$^2$ ............................................. A61K 7/34
[52] U.S. Cl. ........................... 424/66; 424/DIG. 5; 424/65; 424/68; 424/357
[58] Field of Search ................ 424/66, DIG. 5, 66, 424/68, 65, 357

[56] References Cited

U.S. PATENT DOCUMENTS

| | | | |
|---|---|---|---|
| 2,889,253 | 6/1959 | Berger et al. | 424/66 |
| 3,641,239 | 2/1972 | Mohrlok | 424/184 X |
| 3,873,686 | 3/1975 | Beekman | 424/47 |
| 3,903,258 | 9/1975 | Siegal | 424/66 |
| 3,911,105 | 10/1975 | Papantoniou et al. | 424/64 |
| 3,928,557 | 12/1975 | Wright et al. | 424/47 |
| 3,953,591 | 4/1976 | Synder | 424/184 |

FOREIGN PATENT DOCUMENTS

| | | | |
|---|---|---|---|
| 677,857 | 1/1964 | Canada | 424/184 |
| 1,069,982 | 2/1954 | France | 424/184 |
| 844,769 | 9/1961 | France | 424/66 |
| 45-2,915 | 1/1970 | Japan | 424/184 |
| 45-2,916 | 1/1970 | Japan | 424/184 |
| 965,236 | 7/1964 | United Kingdom | 424/184 |

*Primary Examiner*—Dale R. Ore
*Attorney, Agent, or Firm*—Frank T. Barber; Richard G. Harrer

[57] ABSTRACT

A novel combination of powdered materials such as zirconium and aluminum salts suspended in a solid solution of volatile silicones and long chain alcohols. The silicones and alcohols are brought into solid solution by mixing the components in liquid phase at temperatures not to exceed 150° F. (66° C.). The addition of the powdered material to the silicone oil and alcohol matrix prevents the separation of the components upon cooling.

16 Claims, No Drawings

COSMETIC STICK

This application is a continuation-in-part of Ser. No. 655,665, filed Feb. 5, 1976, now abandoned.

BACKGROUND

This invention relates to cosmetic compositions of matter in stick form, particularly to antiperspirant sticks.

In the prior art and in the market place there are solid cosmetic sticks. Solid stick antiperspirants and deodorants having astringent zirconium and aluminum compounds as the active agent are of primary concern and the invention will be treated with particular emphasis on these products, although the inventive concept has wider application to cosmetic sticks in general.

The two principal types of stick antiperspirant on the market heretofore were the solution type and the alcohol in water type. Such sticks have attained a certain degree of popularity but have certain disadvantages along with their good points.

The solution type is hard to the point of being brittle and has a tendency to break off in application. The antiperspirant consumer product is somewhat greasy and tacky due to the large amount of propylene glycol in combination with the aluminum compound.

The alcohol/water stick loses alcohol in prolonged storage, which can impair the acceptability of the product. A disadvantage felt by the user of the alcohol/water formula is a sensation of stinging and coldness on application.

Neither of the prior art market formulations is easy to apply; they are hard and drag on application. The prior art cosmetic formulations generally are of these two formula types.

There is a need for a formulation having a low melting point for easy application and having a smooth and slippery, yet dry feel. Cosmetic ingredients may be found in the prior art which exhibit one or more of the properties desired but combinations of such ingredients which are both efficacious and compatible with each other cannot be predicted. In this case, volatile silicone oils were known to be low staining and have favorable dryness and slip. Long chain alcohols were known to be hard enough to provide a useable stick. However, silicone oils and long chain alcohols in solid form are not compatible. The alcohols solidify and press out the silicone oils as liquid at room temperature. Therefore they had not been used together in a solid stick antiperspirant before this invention.

SUMMARY

We have discovered that by mixing together water-insoluble alcohols and volatile silicone oils at the melting temperature of the alcohols, preferably 130° and 150° F., and adding thereto powdered materials such as metallic astringents, the silicone oils do not separate out upon cooling, contrary to what one might expect and predict, and that the addition of the powdered materials to the matrix thus formed imparts surprising additional strength and hardness to the resulting composition. Surprisingly it potentiates the slip and dryness of feel in the matrix instead of detracting from these properties.

According to one aspect of the invention, powdered astringent salts such as zirconyl hydroxy halides, basic aluminum halides, zirconium aluminum glycine complex, aluminum chlorides and the like, or mixtures thereof, suspended in a solid solution of volatile silicone oils selected from the group consisting of polydimethylcyclosiloxanes having 3 and 6 silicon atoms, linear polydimethylsiloxane having a viscosity of ten (10) centistokes or less (25° C.) and mixtures thereof, and water insoluble alcohols having 16 to 22 carbon atoms in the chain comprise a new and useful solid antiperspirant composition which can be used in stick form. The silicone oils and alcohols are heated together to the melting point of the alcohols but not to exceed 150° F. (66° C.) with the addition of the basic aluminum halide. When the mixture is cooled, the silicone oils and alcohols stay in solution and the powdered astringents add a surprising degree of strength to the matrix.

In terms of weight, the constituents may vary as follows: the alcohols may be from about 15% to about 70% of the total composition; they are preferably 20% to 30% and most preferred 20% of the total composition.

The volatile silicone oils may vary from 10% to 65%, preferably from 50% to 56%. Up to 5% of the non-volatile silicone oils are acceptable.

The amount of astringent employed should be sufficient to provide strength and hardness to the final composition as well as sweat reduction. Although at the present time there are no standards for antiperspirant products vis-a-vis sweat reduction, it has been proposed by the OTC panel commissioned by the United States Food and Drug Administration, that in order for a product to be labeled as an antiperspirant it must provide at least 20% sweat reduction by the so-called "Hot Room Test". It will be appreciated that the various powdered astringents which are useful in our composition do not provide the same degree of antiperspirancy, and thus it is extremely difficult to set the precise minimum amount of powdered astringent required from an efficacy standpoint. For example, it is generally recognized that each of aluminum chlorhydrate and the zirconium salts are excellent antiperspirants, although the zirconium salts are generally more efficacious than the aluminum salts. However, in order to provide the necessary strength, hardness and minimum sweat reduction in an antiperspirant stick, one should employ at least about 10% of the powdered astringent. The amount of astringent employed should not exceed about 40% by weight of the composition, since beyond that level proper mixing does not seem to take place. A typical preferred product will contain approximately 24% by weight of powdered astringent, 56% by weight of volatile silicone oil, and about 20% by weight of long chain alcohols.

Our invention may also include use of powdered materials other than the aforementioned astringents. Thus, any powdered material can be used which is non-reactive with the long chain alcohols and volatile silicones employed and which does not decompose at the melting point of the particular long chain alcohol used to formulate the solid composition. For example, each of talc, sodium bicarbonate, starch, fumed silica and clays may be used in addition to or as a partial or complete replacement of the powdered astringent previously described. All of the foregoing materials are non-reactive with the silicones and alcohols useful in the composition and do not decompose at the melting point of the alcohols, although care should be taken when using sodium bicarbonate since it will decompose to sodium carbonate at relatively low temperatures. Cetyl alcohol is a preferred alcohol when using sodium bicarbonate.

It will be understood that if one replaces any portion or all of the powdered astringent with one or more of the non-astringent powdered materials mentioned above, the antiperspirancy of the final composition will be reduced. However, so long as the final product has at least 2% by weight of powdered astringent, the composition will still be useful as a personal deodorant, although not necessarily as an antiperspirant.

DESCRIPTION OF PREFERRED EMBODIMENTS

EXAMPLE I

A batch of the presently preferred composition of matter, hereafter referred to as No. 71, was made as follows: Polydimethylsiloxanes having 4, 5 and 6 silicon atoms consisting of between 30–40% $D_4$, 60–70% $D_5$, and 1–5% $D_6$ (Dow Corning Corporation trademark DC345 fluid); stearyl alcohol USP grade ($C_{18}H_{37}OH$) (Ashland Chemical Company trade name Adol 62); 5/6 basic aluminum chlorhydrate (Reheis Chemical Company trademark Chlorhydrol Micro-Dry Ultra Fine) were obtained. 1,498.5 pounds of the silicone oil and 540 pounds of stearyl alcohol were added in that order with agitation to a 500 gallon flat-bottom hot water jacketed stainless steel tank equipped with stainless steel fittings. The temperature of the batch was brought to 66° C. (150° F.), taking care not to raise the temperature of the batch above 66° C. Large chunks of stearyl alcohol were broken up with a stainless steel paddle to hasten the melting process. At 56° C. the batch became a clear solution. The process of adding and heating took 3 to 4 hours.

648 pounds of aluminum chlorhydrate were added slowly while not permitting the temperature of the batch to drop below 55° C. (131° F.) and the batch was allowed to mix 1½ hours. Thereafter 13½ pounds of perfume were added and mixing was continued for 15 minutes. Then the batch was cooled to 51° C. (125° F.) by circulating cool water through the jacket of the tank. At this temperature the composition of matter was in liquid phase. Batching time consumed 6 to 8 hours.

The mixture was then fashioned into an antiperspirant stick. The composition was introduced at about 125° F. and solidified by cooling to below 120° F.

EXAMPLE II

Using the procedure of Example I, a silicone oil specified as 99% pure $D_4$ siloxane (obtained from Union Carbide, trademark designation Silicone 7207) was substituted for DC-345.

EXAMPLE III

Using the procedure of Example I, a silicone specified as 95% pure $D_5$ siloxane (made by Union Carbide, trademark Silicone 7158) was substituted for DC-345.

All three formulations are acceptable. The 7207 silicone formulation gives a drier appearance on the skin. The silicone 7158 and DC-345 formulations are essentially the same, but the combination of $D_4$, $D_5$ and $D_6$ per Example I (DC-345) produces the best cosmetic properties of the group.

The efficacies of various types of products were compared with the following results:

TABLE I

| Test Sample | Sweat Reduction |
|---|---|
| No. 71 | 33.8 ± 4.3% |
|  | 36.9 ± 4.7% |
| *Product F | 28.5 ± 4.7% |
| +Product C | 18.7 ± 3.6% |

TABLE I-continued

| Test Sample | Sweat Reduction |
|---|---|
| *Product D | 32.6 ± 3.6% |

*solution type
+alcohol in water type

The same standard efficacy procedure was used in each case.

On testing for sterility, No. 71 was found not to support bacterial growth.

A preferred formulation, i.e., DC-345, 55.5%; stearyl alcohol, 20.0%; aluminum chlorhydrate, 24%; perfume, 0.5% total, 100% is cosmetically acceptable with respect to dryness, slip and ease of application. The staining level compares favorably to average staining levels of most aerosol antiperspirants and efficacy is equal to, if not superior to, most antiperspirants, aerosols, roll-ons or sticks.

EXAMPLE IV

Using the procedure of Example I, 8.1 pounds of glycerol monostearate and 81 pounds of talcum powder replace 89.1 pounds of DC-345. The glycerol monostearate is added with the stearyl alcohol and the talcum powder is added with the aluminum chlorhydrate.

The glycerol monostearate may be added to make the crystal structure more uniform and may conveniently comprise from 0.1 to 1.0% of the stick. In that event, the astringent's stabilization effect should be augmented. This can be inexpensively accomplished without losing the desired efficacy by means of the addition of about 1% to 10% (by weight of the stick) talc or other nonreactive powder such as fumed silica and clays.

EXAMPLE V

A composition was prepared using the following formula:

| Ingredient | % by weight |
|---|---|
| Dimethylcyclosiloxane | 51 |
| Cetyl alcohol | 24 |
| Glycerolmonostearate | 1 |
| Fumed silica | 1 |
| Talc | 3 |
| NaHCO$_3$ | 20 |

Although this product is not an antiperspirant it can be used as a personal deodorant.

EXAMPLE VI

An antiperspirant composition was prepared according to the following formula:

| Ingredient | Weight % |
|---|---|
| *Straight chain siloxane having a viscosity of 0.65 centistokes | 50.5 |
| Stearyl alcohol | 22.0 |
| Glycerolmonostearate | 0.5 |
| Aluminum chlorhydrate | 24.0 |
| Talc | 3.0 |
|  | 100.0 |

*can be obtained from Dow-Corning under the trademark Dow-Corning 200.

Various astringents in powder form may be utilized in the invention; for example, the basic aluminum halides wherein "basic" refers not to pH but to the number of hydroxy radicals substituted for halide atoms. Five-sixths basic aluminum chlorhydrate having the formula $Al_2(OH)_5Cl$, a well known and widely used astringent, is preferred. Sodium aluminum lactate, on the other hand, does not work because it cannot be powdered. Zirconium, aluminum and hafnium salts buffered in various ways and finely powdered are generally useful in this invention. Such astringents are presently known to the art.

It is to be understood that the products and processes of the invention may be modified in light of the teachings of this diclosure, all of which are within the scope of the invention which is to be measured by the appended claims read in light of the specifications.

We claim:

1. A solid composition comprising about 15% to 40% of a powdered material suspended in a solid matrix comprising from 10% to 65% of one or more volatile silicone oils selected from the group consisting of a polydimethylcyclosiloxane having 3 to 6 silicon atoms and a linear polydimethylsiloxane having a viscosity of ten centistokes or less at 25° C. and mixtures thereof, and from 15% to 70% of at least one long chain water insoluble aliphatic alcohol having 16 to 22 carbon atoms in the chain, said powdered material being non-reactive with said long chain alcohol and volatile silicones and which does not decompose at the melting point of said alcohol.

2. The composition of claim 1 wherein the powdered material is an astringent metallic salt selected from the group consisting of a basic aluminum halide, a zirconyl hydroxy halide, and a zirconium aluminum glycine complex.

3. The composition of claim 2 wherein the astringent metallic salt is 5/6 basic aluminum chlorhydrate.

4. The composition of claim 2 wherein the astringent metallic salt is zirconyl hydroxy chloride.

5. The composition of claim 2 wherein the astringent metallic salt is zirconium aluminum glycine complex.

6. The composition of claim 2 wherein the volatile silicone comprise a mixture of $D_4:D_5:D_6$ polydimethylcyclosiloxanes in the proportions $D_4 = 30-40\%$; $D_5 = 60-70\%$; $D_6 = 1-5\%$.

7. The composition of claim 1 wherein the alcohol is stearyl alcohol.

8. The composition of claim 1 wherein the alcohol is about 20 to 30% and the silicone oil is about 50 to 56% by weight.

9. The composition of claim 2 comprising 24% powdered astringent, 56% volatile silicone oil, and 20% alcohol.

10. The composition of claim 9 wherein the astringent is aluminum chlorhydrate, the volatile silicone oil is a mixture of $D_4$, $D_5$ and $D_6$ polydimethylcyclosiloxanes about the ratio 35:60:5, and the alcohol is stearyl alcohol.

11. The composition of claim 1 where the powder is sodium bicarbonate.

12. The composition of claim 1 wherein the powder is talcum powder.

13. The composition of claim 9 wherein about 0.1 to 1.0% of the total composition is glycerol monostearate and about 1% to 10% of the total composition is a non-reactive, non-astringent powder.

14. The composition of claim 13 wherein the powder is talc.

15. A solid stick antiperspirant composition comprising about 10% to 40% of at least one astringent metallic salt present in powder form suspended in a solid matrix comprising from 10% to 65% of a volatile silicone selected from the group consisting of a polydimethylcyclosiloxanes having 3 to 6 silicon atoms and a linear polydimethylsiloxanes having a viscosity of ten centistokes or less at 25° C. and mixtures thereof, and from about 15% to about 70% of at least one water insoluble aliphatic alcohol having 16 to 22 carbon atoms in the chain.

16. The method of making a stable stick antiperspirant comprising heating and mixing a water-insoluble aliphatic alcohol having 16 to 22 carbon atoms in the chain and a volatile silicone selected from the group consisting of a polydimethylcyclosiloxane having 3 to 6 silicon atoms and a linear polydimethylsiloxane having a viscosity of ten centistokes or less at 25° C. and mixtures thereof together at the melting temperature of the alcohol not to exceed 150° F., adding a powdered metallic astringent, and allowing the resultant product to solidify by cooling.

* * * * *